(12) United States Patent
Lee et al.

(10) Patent No.: US 7,309,504 B2
(45) Date of Patent: Dec. 18, 2007

(54) **EXTRACT OF *ACANTHOPANAX KOREANUM* FOR THE TREATMENT OR PREVENTION OF HEPATITIS OR THE LIVER PROTECTIVE DRUG**

(75) Inventors: Jung Joon Lee, Taejeon-si (KR); Jeong-Hyung Lee, Taejeon-si (KR); Young Soo Hong, Taejeon-si (KR); Young Ho Kim, Taejeon-si (KR); Jeong Bum Nam, Taejeon-si (KR); Dong Hwan Shon, Jeollabuk-do (KR); Hang Sub Kim, Taejeon-si (KR)

(73) Assignee: Korea Research Institute of Bioscience and Biotechnology (KR)

( * ) Notice: Subject to any disclaimer, the term of this patent is extended or adjusted under 35 U.S.C. 154(b) by 0 days.

(21) Appl. No.: 10/502,140

(22) PCT Filed: Jan. 24, 2003

(86) PCT No.: PCT/KR03/00155

§ 371 (c)(1),
(2), (4) Date: Jul. 19, 2004

(87) PCT Pub. No.: WO03/061553

PCT Pub. Date: Jul. 31, 2003

(65) Prior Publication Data

US 2005/0089586 A1    Apr. 28, 2005

(30) Foreign Application Priority Data

Jan. 25, 2002    (KR) ................. 10-2002-0004553

(51) Int. Cl.
*A61K 36/25* (2006.01)
*A61K 36/00* (2006.01)

(52) U.S. Cl. .................. 424/728; 424/773; 424/779

(58) Field of Classification Search ............... None
See application file for complete search history.

(56) References Cited

U.S. PATENT DOCUMENTS

| | | | |
|---|---|---|---|
| 5,900,434 A | 5/1999 | Pyun et al. | |
| 6,365,768 B1 * | 4/2002 | Palladino et al. | 560/117 |
| 6,365,798 B1 | 4/2002 | Brown | |
| 6,593,363 B1 * | 7/2003 | Suh et al. | 514/510 |
| 2003/0143290 A1 * | 7/2003 | Cho et al. | 424/728 |
| 2004/0142047 A1 * | 7/2004 | Yoon et al. | 424/728 |

FOREIGN PATENT DOCUMENTS

| | | |
|---|---|---|
| KR | 00241269 | 11/1999 |
| KR | 2001060837 | * 7/2001 |
| KR | 2001060838 | * 7/2001 |
| KR | 1020030043191 | 6/2003 |

OTHER PUBLICATIONS

J.N. Eloff; "Which extractant should be used for the screening and isolation of antimicrobial components from plants?" Journal of Ethnopharmacology, 60, (1998) pp. 1-8.*

Choi, in Pyo et al., Studies on Development of novel functional biologicalmolecules: Investigation of Mechanism of actions and regulatory molecules of inflammatory cytokines Summary in English only.

Tong L et al., Effects of plant polysaccharides on cell proliferation and cell membrane contents of sialic acid, phospholipid and cholesterol in S 180 K 562 cells'. IN: Zhon.

An article entitled "Pimaradiene Diterpenes From *Acanthopanax koreanum*", By Kim et al., published by Journal of Natural Products, vol. 51, No. 6 pp. 1080-1083, Nov.-Dec. 1988).

An article entitled "Antioxidant and Hepatoprotective . . . ", By Lin et al., published by Pytotherapy Research, vol. 14, pp. 489-494, (2000).

An article entitled "New Hepatoprotective saponins, Bupleurosides . . . ", By Matsuda et al., published by Bioorganic & Medicinal Chemistry Letters, vol. 7, No. 17, pp. 2193-2198.

American Chemical Society, Registry No. 119290-87-8, for Acanthoic Acid (Chemical Abstract Series), Feb. 24, 2006.

* cited by examiner

*Primary Examiner*—Christopher R. Tate
(74) *Attorney, Agent, or Firm*—Bachman & LaPointe, P.C.

(57) ABSTRACT

The disclosure concerns an extract of *Acanthopanax koreanum* and its use. More particularly, it concerns the extract of *Acanthopanax koreanum* comprising 1) the extract of *Acanthopanax koreanum* extracted from water, 2) among the water extract, the extract of *Acanthopanax koreanum* only containing ethanol insoluble part obtained by precipitating ethanol, 3) among the ethanol insoluble part, the extract of *Acanthopanax koreanum* containing polysaccaride with a molecular weight larger than range of 12,000~14,000, or 4) among the ethanol insoluble part, the extract of *Acanthopanax koreanum* containing polysaccaride with a molecular weight larger than 100,000, which is respectively obtained from the root or stem of *Acanthopanax koreanum*. The extract of the present invention shows a high inhibitory activity against hepatitis and protects the liver, and thus, can be used for the treatment or prevention of hepatitis, or as a liver protective drug.

7 Claims, 11 Drawing Sheets

EXTRACT OF *ACANTHOPANAX KOREANUM* FOR THE TREATMENT OR PREVENTION OF HEPATITIS OR THE LIVER PROTECTIVE DRUG

FIELD OF THE INVENTION

The present invention relates to an extract of *Acanthopanax koreanum* for the treatment or prevention of hepatitis or the liver protective drug and its use.

BACKGROUND OF THE INVENTION

Located between the digestive system and body circulating system in human body, liver plays an important role in defending our body from the harmful intrusion of toxic substances and in metabolism. Since foreign substances intruded into human body first passes through the liver, liver has a high possibility to be exposed to various toxic substances other than nutrients, and thus, has a higher possibility to be injured than other internal organs.

As an internal organ with excellent restoration ability, liver can completely recover its functions in slight damages. However, if liver is continuously damaged by alcohol over ingestion, chemical substance abuse, viral hepatitis, and bile secretion suspension, not only its functions are deteriorated, but a part of liver tissues are completely damaged, and the thus damaged part cannot be completely restored, which goes through liver fibrosis and may finally advance into fatal cirrhosis. Further, liver diseases do not show any pains or subjective symptoms at the initial stage, but they are found at the terminal stage. Therefore, it is impossible to treat liver diseases at a proper stage, and thus, liver diseases show a high death rate.

Regardless of the severity of liver diseases, an effective liver-disease therapeutic has not yet been found. As for liver diseases caused by viral hepatitis, anti-virus drugs are being used, but their side effects cause serious problems. As for liver diseases caused by toxic substances recently increasing due to alcohol and environment pollution, an effective liver disease therapeutic has not yet been found. Accordingly, the development of a drug, which treats and prevents liver damage while maintaining the structure and function of liver tissue is keenly required. However, since no experimental method has been developed till now, there are many limitations in developing a liver disease therapeutic. That is, in fact, there is not enough experimental support on the drugs referred to as liver protective drugs.

However, recently, an animal model has been developed which contributed to the development of a liver disease therapeutic. In this connection, an animal model induced with carbon tetrachloride is used in order to develop a liver disease therapeutic caused by toxic substances, and an acute hepatitis model induced with D-galactosamine (hereinafter abbreviated into "D-GalN") and lipopolysaccharide (hereinafter abbreviated into "LPS") are used in order to develop a liver disease therapeutic caused by virus.

Especially, since the above liver damage model induced with D-GalN/LPS causes liver damage by the immune reaction which is actually proceeded in most liver diseases, it is the animal model appropriate for the treatment and prevention of liver diseases [Ken-Ichiro Kosai, Kunio Matsumoto, Hiroshi Funakoshi and Toshikazu Nakamura, Hepatocyte Growth factor Prevents Endotoxin-induced Lethal Hepatic Failure in Mice. *Hepatology*, 1999, 30, 151-159]. In acute hepatitis model induced with D-GalN/LPS, D-GalN inhibits RNA synthesis and protein synthesis in cells to maximize liver toxicity caused by LPS, and LPS promotes the secretion and synthesis of cytokine, nitrogen monoxide (NO) and active oxygen of the kupffer cell, which is the macrophage of liver. It has been found out that tumor necrosis factor alpha (TNF-α) induced by excessive nitrogen monoxide is a main etiological agent of septicemia or acute hepatitis. In fact, it has been found out that TNF-α causes in vivo and in vitro hepatocyte death [Michael D Josephs, F. Rena Bahjat, Kunitaro Fukuzuka, Riadh Ksontini, Carmen C. Solorzano, Carl K. Edwards III, Cynthia L. Tannahill, Sally L. D. MacKAY, Edward M. Copeland III, and Lyle L. Moldawer. Lipopolysaccharde and D-galactosamine-induced hepatic injury is mediated by TNF-a and not by Fas ligand. *Am J Physiol Regulatory Integrative comp Physiol*, 2000, 278, R1196-R1201]. Further, Leist considers TNF-α to be the most important factor in causing liver damage by proving that the mortality is decreased when the acute liver damage model induced with D-GalN/LPS is treated with anti-tumor necrosis factor alpha (anti-TNF-α) [Leist M. Gauntner F., Bohlinger I, Germann P G, Tiegs G, Wendal A. Murine hepatocytee apoptosis induced in vitro and in vivo by TNF-α requires transcriptional arrest. *J. Immunol.* 1994, 153, 1778-1788].

The cell death process is largely affected by Bcl-2 family (pro- and anti-apoptotic member) proteins, which can be exemplified by Bax protein or Bid protein [Yongge Zhao, Shuchen Li, Erin E. Childs, Diane K. Kuharsky, and Xiao-Ming Yin. Activation of Pro-death Bcl-2 Family Proteins and Mitochondria Apoptosis Pathway in Tumor Necrosis Factor-a-induced Liver Injury. *J. Biol. Chem.* 2001, 276, 27432-27440].

More particularly, the death process of hepatocyte activates caspase 8 by interacting with FADD or TRADD protein having a death domain, when proteins inducing apoptosis such as TNF bind to the cell receptor, TNF receptor 1. The thus activated caspase 8 cleaves Bid protein and transforms it into an activated form, tBid. The thus transformed tBid is translocated to mitochondria to cause cytchrome C release. The thus released cytchrome C activates pro-caspase 9 into caspase 9, and this caspase 9 induces the cooperative effects of lower caspases by activating caspase 3 which leads all cells to apoptosis [Xiao-Ming Yin, Bid, a critical mediator for apoptosis induced by the activation of Fas/TNF-R1 death receptors in hepatocytes. *J. Mol,* 2000, 78, 203-211].

Therefore, hepatocyte apoptosis generated in acute liver-injury model induced with D-GalN/LPS causes the activation of apoptosis pathway by TNF-α receptor. Accordingly, it can be proved that an extract of the stem or root of *Acanthopanax koreanum* activates liver protection by the said working by examining whether *Acanthopanax koreanum* polysaccharide inhibits TNF-α activity itself, and by proving that *Acanthopanax koreanum* polysaccharide inhibits the expression of the important protein activated by TNF-α.

In addition, the amount of circulating alanine aminotransferase (hereinafter abbreviated into ALT, GPT index) and aspartate aminotranasferase (hereinafter abbreviated into AST, GOT index), and the concentration of circulating tumor necrosis factor (TNF-α) are measured to determine liver protection activity in the acute liver damage model induced with D-GalN/LPS. In addition, the liver protection effect of the sample can be determined more precisely by measuring apoptosis inhibition effect of hepatocyte using the activity inhibiting hepatocyte DNA cleavage as an index, and by measuring the 24 hour survival rate of the mouse.

Recently a drug for the treatment or prevention of hepatitis by protecting the liver functions by using the said animal model is being developed. Especially, it has been reported that saponin, bupleuroside compounds (H. Maysuda et al., *Bioorg. Med. Chem.*, 1997, 7, 2193-2198), naringin (K. Kawaguchi et al., *Eur. J. Pharmacol.*, 1999, 368, 245-250), green tea extract(P. HE et al., *J. Nutr.*, 2001, 131, 1560-1567), polysaccharides extracted from the seeds of *Celosia argentea* show activity in protecting the liver functions in the liver damage model induced with D-GalN/LPS and inhibiting the experimental animal lethality (K. Hase et al., *Biol, Pharm. Bull.*, 1996, 19, 567-572).

In addition, there is a report on the liver protection activity of an extract of *Acanthopanax senticosus* [Chun-Ching Lin and Pei-Chen Huang, *Phytotherapy Research*, 2000, 14, 489-494]. However, no specific examples on an extract of *Acanthopanax koreanum* for the treatment or prevention of hepatitis or liver protection have been reported. *Acanthopanax senticosus* morphologically differs a lot from *Acanthopanax koreanum*. *Acanthopanax senticosus* is thickly wooded with thin long thorns on its bark and branches, and the style of the fruit is divided into 5. Further, it is mainly distributed in the alpine regions of Korea; Hokkaido, Japan; the Heilung Riverside, China; and Siberia, Russia. *Acanthopanax koreanum* is wooded with triangle shaped grayed-brown thorns with a large base, and the style of its fruit is divided into 2. Further, it is a Korean indigenous plant distributed in the southern part of Korea including Chejudo.

Further, *Acanthopanax koreanum* comprises acanthoic acid; pimara-9(11)-dien-19 oic acid as its main component, whereas, *Acanthopanax senticosus* does not comprise such component [Young H. Kim and Bo S. Chung *J. Nat. Prod.* 1988, 51 1080-1083].

Therefore, in connection with liver diseases caused by hepatitis virus and toxic substances, inventors have devoted themselves in developing a liver disease therapeutic with less side effects, and based on the working model of the acute liver-injury induced with D-GalN/LPS the present invention has been completed by proving an accurate experimental method and results that an extract from the root or stem of *Acanthopanax koreanum* is effective on the treatment and prevention of liver damage while maintaining the structure and function of the liver tissues.

SUMMARY OF THE INVENTION

It is an object of the present invention to provide an extract of *Acanthopanax koreanum* for the treatment or prevention of hepatitis or the liver protective drug.

It is another object of the present invention to provide a use wherein an extract of *Acanthopanax koreanum* can be used for the treatment or prevention of hepatitis or as a liver protective drug on the basis of the working model of the acute liver-injury mice induced with D-GalN/LPS.

BEST MODE FOR CARRYING OUT THE INVENTION

Figure 4:
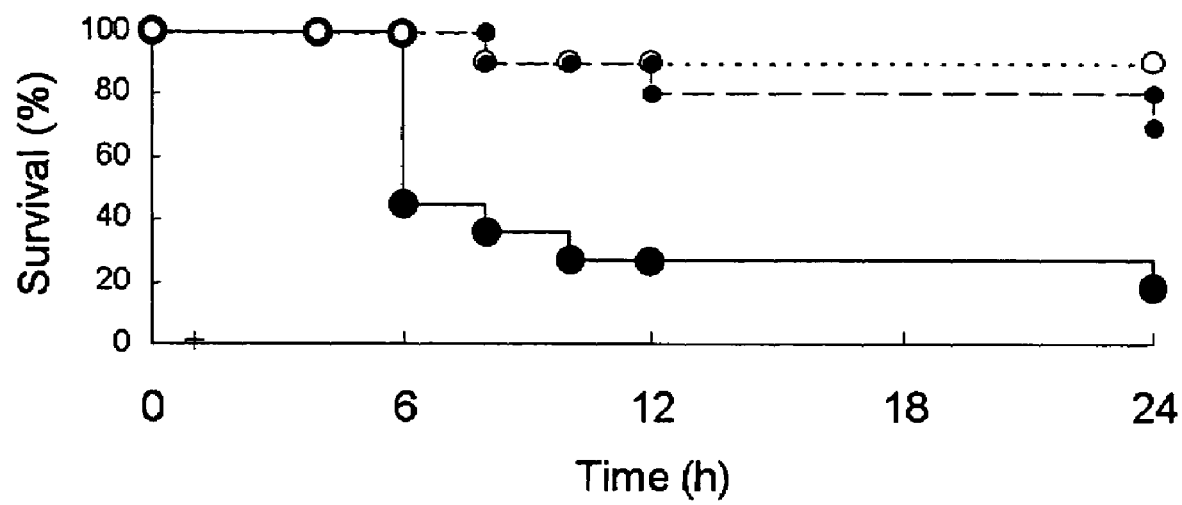
Figure 5:
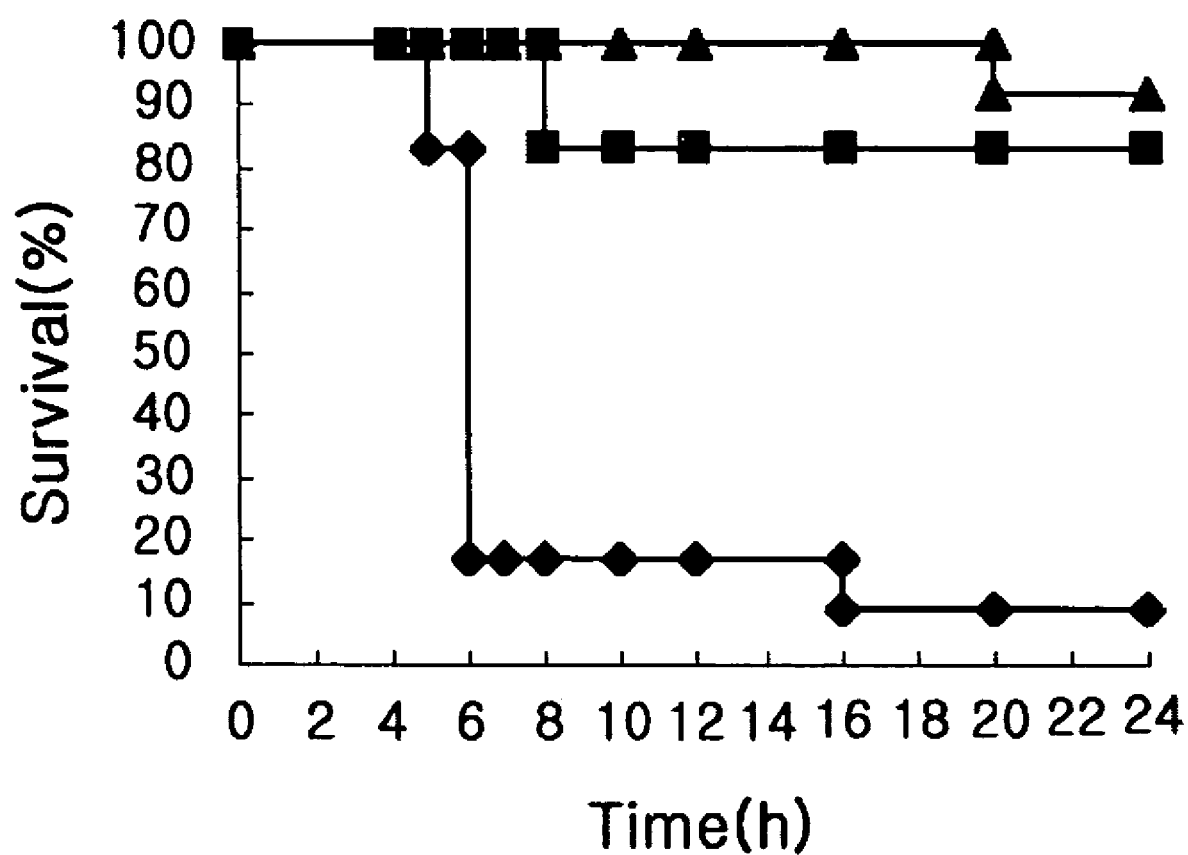

☐ a group treated with the water extract of *Acanthopanax koreanum* root (hereinafter abbreviated into "SRW", 300 mg/kg);

☐ a group treated with the 80%-ethanol insoluble part of the water extract of *Acanthopanax koreanum* root (hereinafter abbreviated into "SRWB", 300 mg/kg); and ● a group treated with physiological saline solution FIG. 4 shows effect of the extract obtained from the stem of *Acanthopanax koreanum*, on the survival of mice in liver-injury model induced by D-GalN/LPS ☐ a group treated with the water extract of *Acanthopanax koreanum* stem (hereinafter abbreviated into "SSW", 300 mg/kg);

☐ a group treated with the 80%-ethanol insoluble part of the water extract of *Acanthopanax koreanum* stem (hereinafter abbreviated into "SSWB", 300 mg/kg); and ● a group treated with physiological saline solution FIG. 5 shows effect of the fraction containing polysaccharide with a molecular weight larger than 100,000, among the said 80%-ethanol insoluble part obtained from the stem of *Acanthopanax koreanum*, on the survival of mice in liver-injury model induced by D-GalN/LPS.

Figure 6:
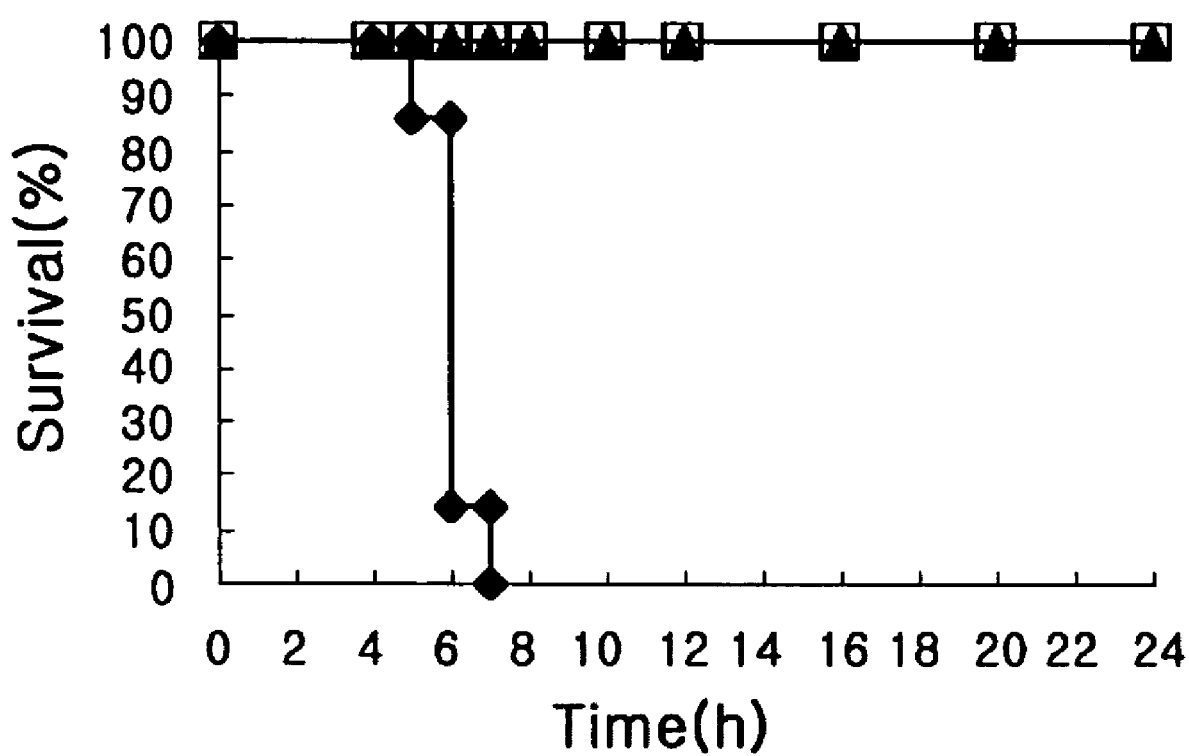

■ a group treated with the fraction containing polysaccharide with a molecular weight larger than 100,000, obtained from the stem of *Acanthopanax koreanum* (30 mg/kg);

▲ a group treated with the fraction containing polysaccharide with a molecular weight larger than 100,000, obtained from the stem of *Acanthopanax koreanum* group (100 mg/kg); and ♦ a group treated with physiological saline solution FIG. 6 shows effect of the fraction containing polysaccharide with a molecular weight larger than 100,000, among the said 80%-ethanol insoluble part obtained from the root of *Acanthopanax koreanum* on the survival of mice in liver-injury model induced by D-GalN/LPS.

☐ a group treated with the fraction containing polysaccharide with a molecular weight larger than 100,000, obtained from the root of *Acanthopanax koreanum* (30 mg/kg)

Figure 7:
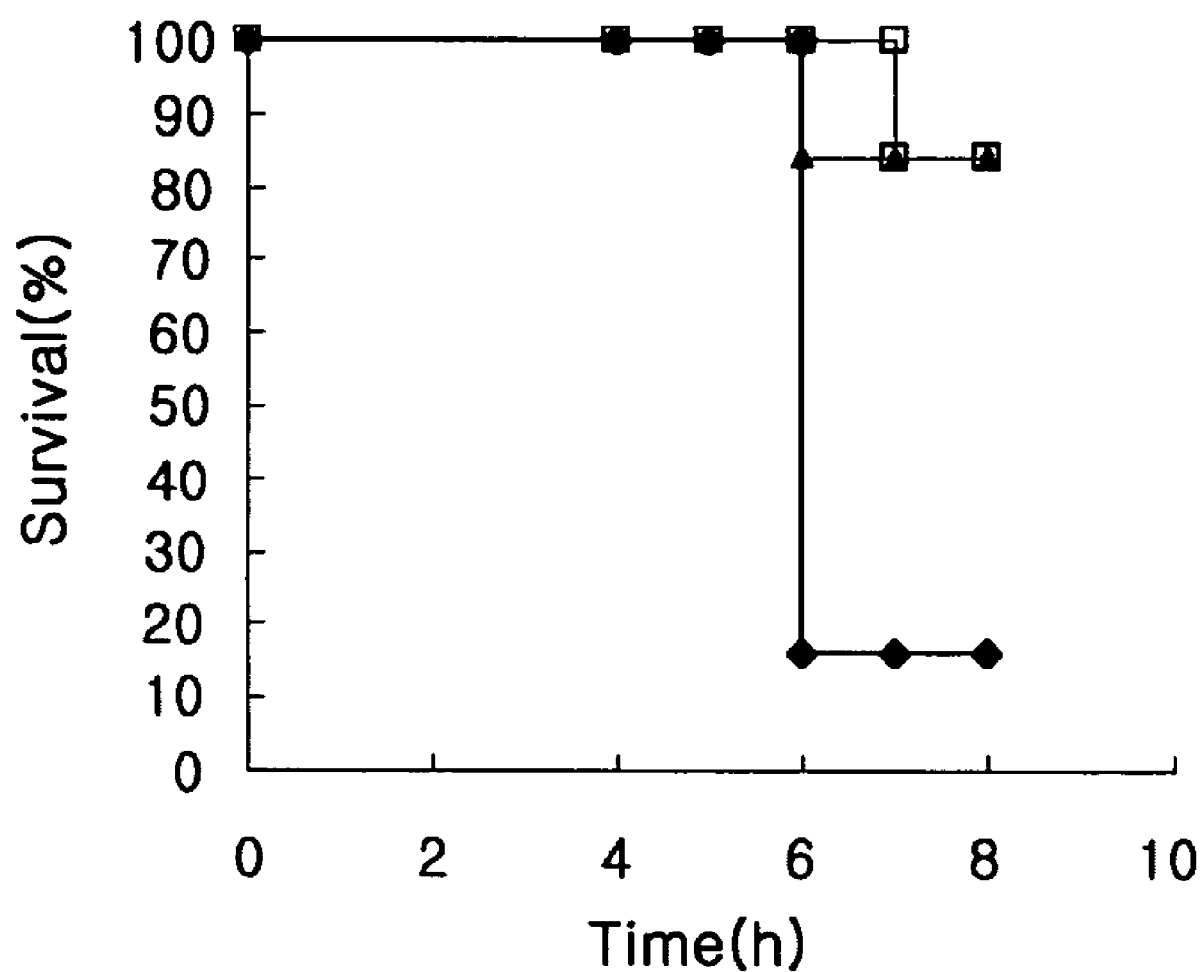

▲ a group treated with the fraction containing polysaccharide with a molecular weight larger than 100,000, obtained from the root of *Acanthopanax koreanum* (100 mg/kg);and ♦ a group treated with physiological saline solution FIG. 7 shows effect of the extract obtained from the root or stem of *Acanthopanax koreanum*, on the survival of mice in liver-injury model induced by D-GalN/TND-α.

☐ a group treated with the fraction containing polysaccharide with a molecular weight larger than 100,000, obtained from the stem of *Acanthopanax koreanum* (100 mg/kg)

Figure 8:
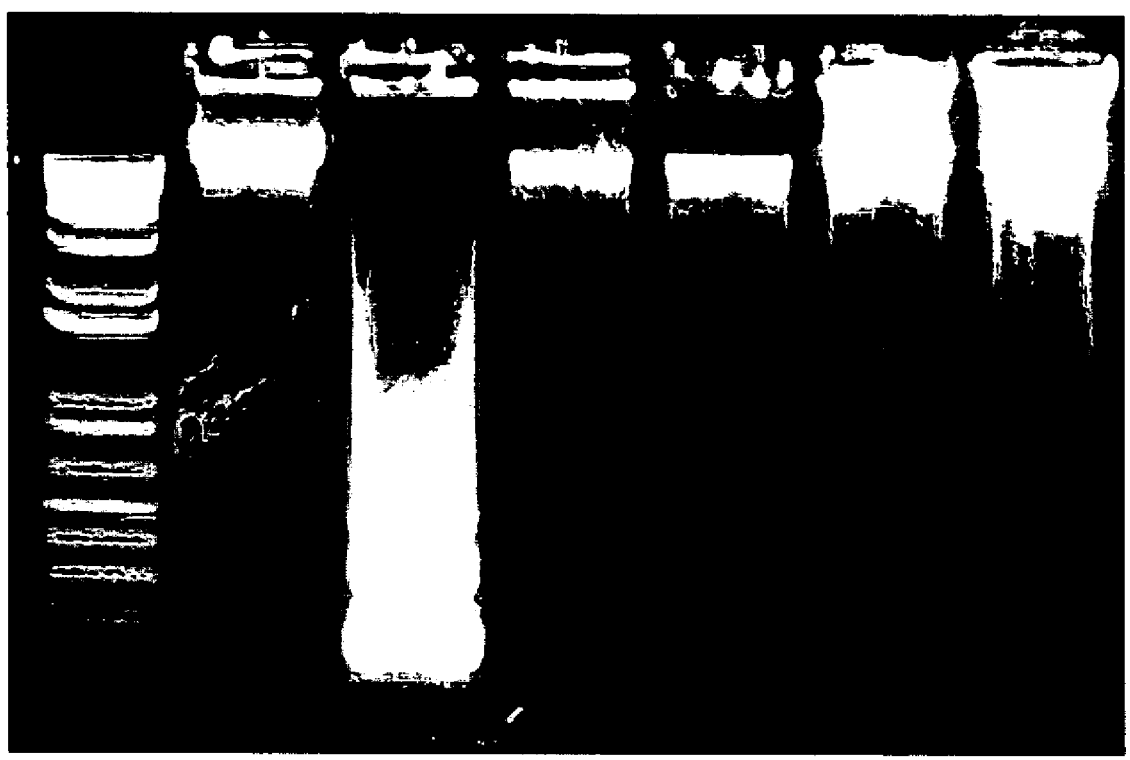

▲ a group treated with the fraction containing polysaccharide with a molecular weight larger than 100,000, obtained from the root of *Acanthopanax koreanum* (100 mg/kg);and ♦ a group treated with physiological saline solution FIG. 8 shows effect of the extract on the DNA fragmentation of liver cell in liver-injury model induced by D-GalN/LPS.

Marker: comparative marker

1: DNA isolated from the liver of the mice to which physiological saline solution was administered.

2: DNA isolated from the liver of the mice to which physiological saline solution was administered after administration of D-GalN/LPS.

3: DNA isolated from the liver of the mice to which D-GalN/LPS and 300 mg/kg of the water extract obtained from the root of *Acanthopanax koreanum* were administered.

4: DNA isolated from the liver of the mice to which D-GalN/LPS and 300 mg/kg of the water extract obtained from the stem of *Acanthopanax koreanum* were administered.

5: DNA isolated from the liver of the mice to which D-GalN/LPS and 300 mg/kg of the 80%-ethanol insoluble part of the water extract obtained from the stem of *Acanthopanax koreanum* were adminstered.

6: DNA isolated from the liver of the mice to which D-GalN/LPS and the fraction containing polysaccharide with a molecular weight larger than range of 12,000~14,000, obtained by dialyzing the said 80%-ethanol insoluble part were administered.

Figure 9:
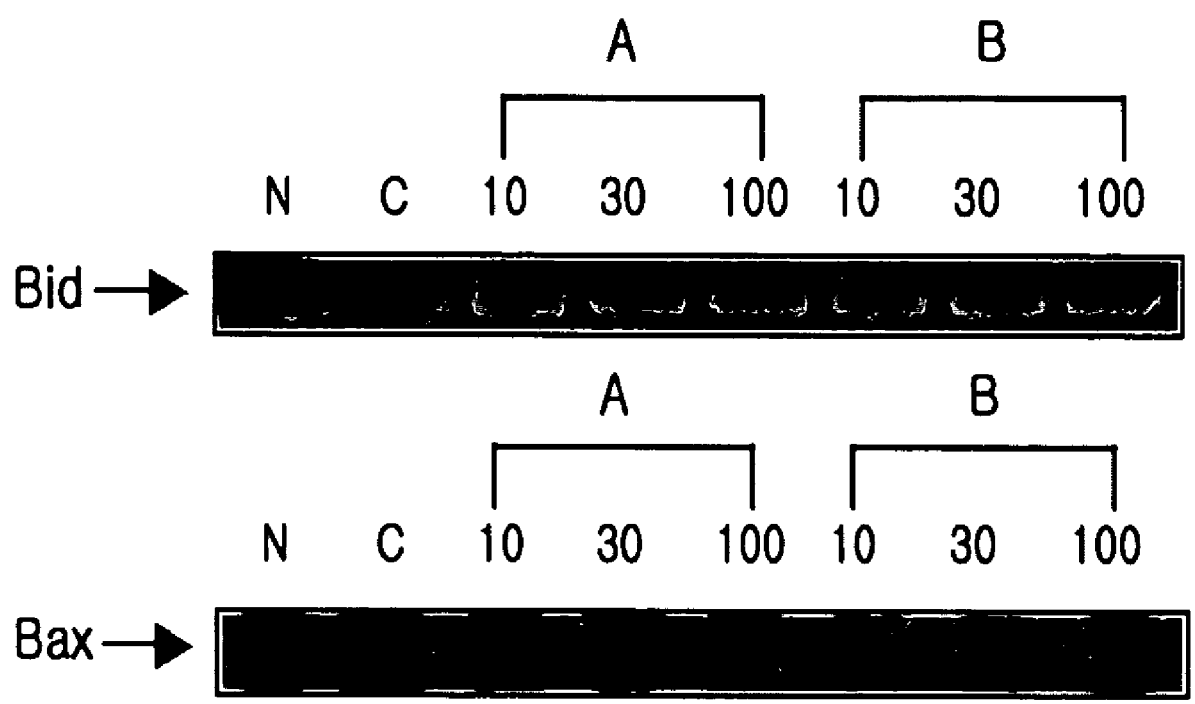

FIG. 9 shows effect of the fraction containing polysaccharide with a molecular weight larger than 100,000, among the ethanol insoluble part on the expression of pro-apoptotic protein;

A: the extract obtained from the stem of *Acanthopanax koreanum*

B: the extract obtained from the root of *Acanthopanax koreanum*

Figure 10:
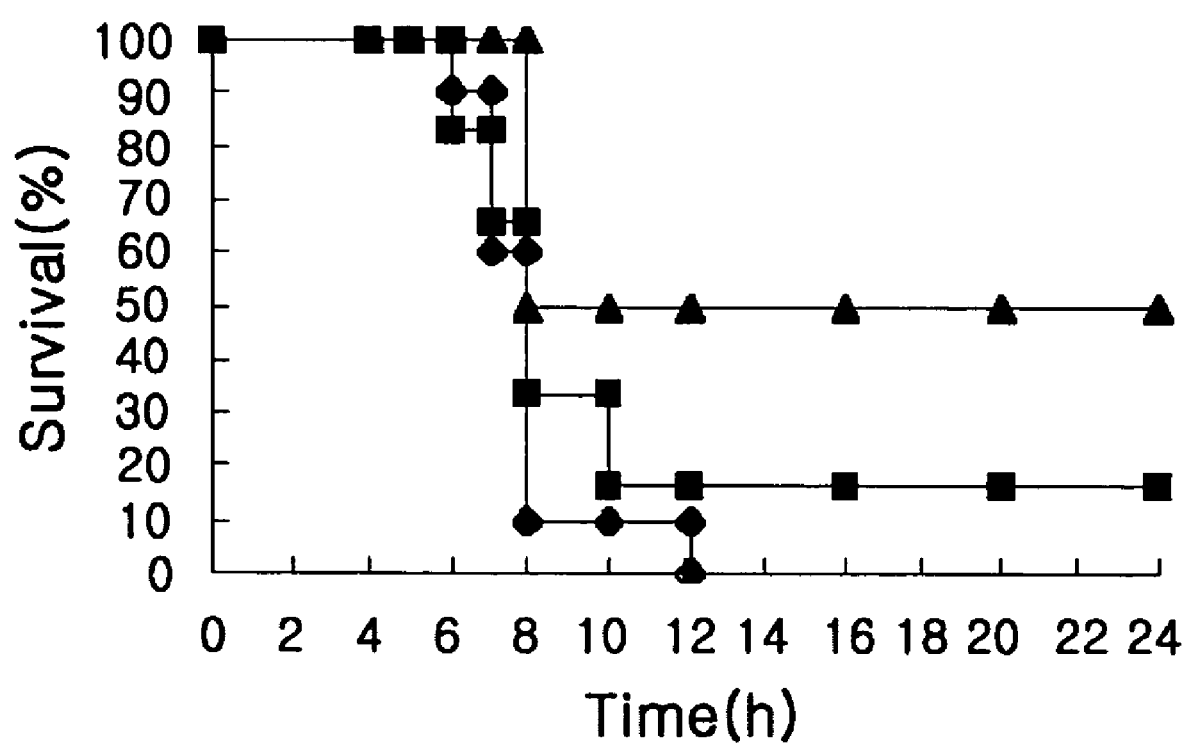

FIG. 10 shows effect of the oral administration of the 80%-ethanol insoluble part of the water extract obtained from the stem of *Acanthopanax koreanum* on the liver protection.

Figure 11:
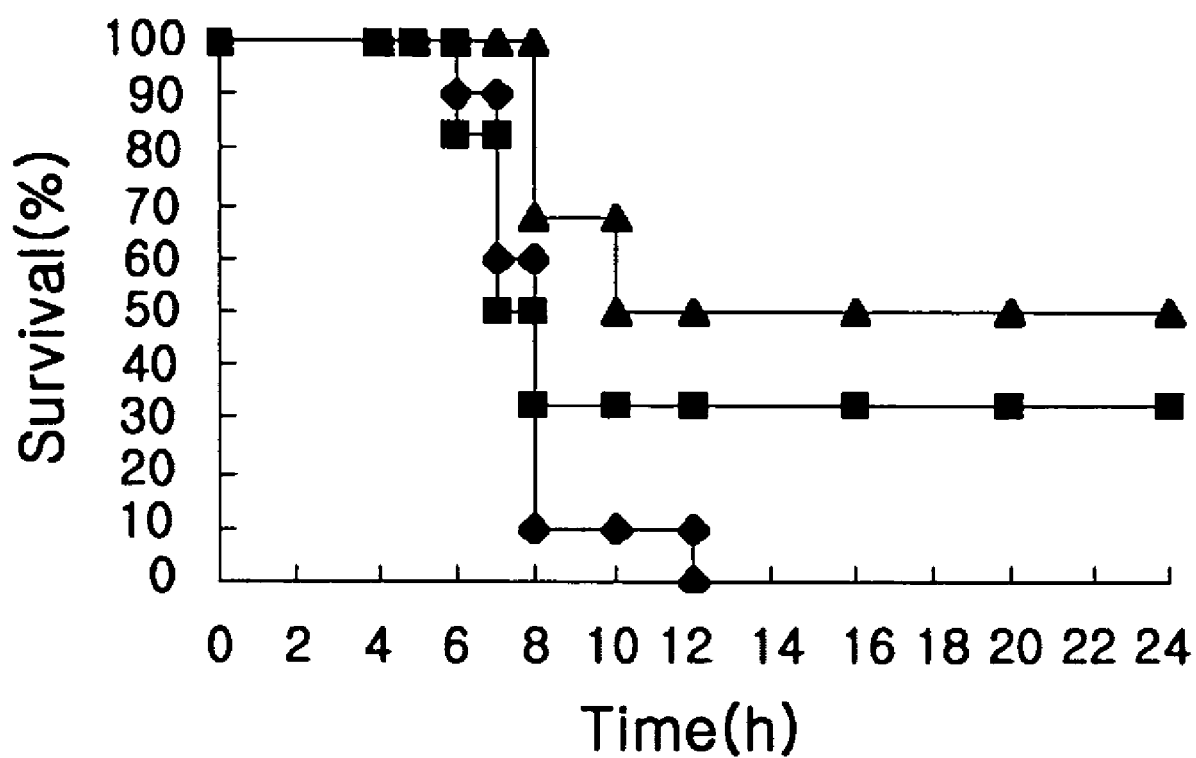

FIG. 11 shows effect of the oral administration of the ethanol insoluble part of the water extract obtained from the root of *Acanthopanax koreanum* on the liver protection.

▲: a group treated with the 80%-ethanol insoluble part of the water extract obtained from the stem or root of *Acanthopanax koreanum* (30 mg/kg)

☐: a group treated with the 80%-ethanol insoluble part of the water extract obtained from the stem or root of *Acanthopanax koreanum* (100 mg/kg); and ◆ a group treated with physiological saline solution The present invention provides an extract of *Acanthopanax koreanum* for the treatment or prevention of hepatitis, or as a liver protective drug.

The extract of the present invention includeds 1) the water extract of the root or stem of *Acanthopanax koreanum* 2) the ethanol insoluble part among the said water extract, obtained by treating the said water extract with ethanol, 3) the fraction containing polysaccharide with a molecular weight larger than range of 12,000~14,000, among the said ethanol insoluble part, or 4) the fraction containing polysaccharide with a molecular weight larger than 100,000, among the said ethanol insoluble part.

Furthermore, the present invention provides a use of the extract obtained from the root or stem of *Acanthopanax koreanum*, as a therapeutic agent for treatment or preventer of hepatitis, or a liver protective drug.

The extract of the present invention inhibits activity of TNF-α and expression of important protein activated by TNF-α in acute liver-injury mice model induced by D-GalN/LPS. Also, the extract of the present invention made high survival rate maintained in the experiment for measurement of lethality rate progressed for 24 hours. Therefore, based on the working model of the acute liver-injury mice induced by D-GalN/LPS, the extract of the present invention can be used as a therapeutic agent or preventer of the hepatitis, or a liver protective drug.

The present invention uses *Acanthopanax koreanum* of which the place of origin is KOREA. The known extract of *Acanthopanax* sp. relates to the extract of the stem or leaves of *Acanthopanax senticosus*. Furthermore, to apply *Acanthopanax senticosus* to experimental or drug material, it must be withered up. However, in the present invention, the extract of *Acanthopanax koreanum* obtained from the root of the *Acanthopanax koreanum* has the same efficiency as one obtained from the stem thereof. Therefore, *Acanthopanax koreanum* does not have to be withered up.

The said water extract of *Acanthopanax koreanum* is prepared by treating the root or stem of *Acanthopanax koreanum* with water by the method such as dipping, maceration or heating. Preferably, the said water extract is prepared by heating the root or stem of *Acanthopanax koreanum* at the temperature higher than 90° C.

The ethanol insoluble part of the said water extract is prepared by treating the said water extract of *Acanthopanax koreanum* with ethanol, of which the final concentration of ethanol is 50~90%. Preferably, the concentration is 75~85%, more preferably 80%.

The fraction containing polysaccharide with a molecular weight larger than range of 12,000~14,000, or larger than 100,000, among the said ethanol insoluble part is prepared by dialysis of the said extract through dialyzing diaphagram or filter membrane corresponding to the molecular weight, respectively.

As shown in the experiment using liver injury mice model induced by D-GalN/LPS, the said water extract of *Acanthopanax koreanum* of the present invention, preferably the said ethanol insoluble part, more preferably the fraction containing polysaccharide with a molecular weight larger than range of 12,000~14,000, or larger than 100,000, among the said ethanol insoluble part has an excellent efficiency for the treatment or prevention of hepatitis, or a liver protective drug.

Figure 3:
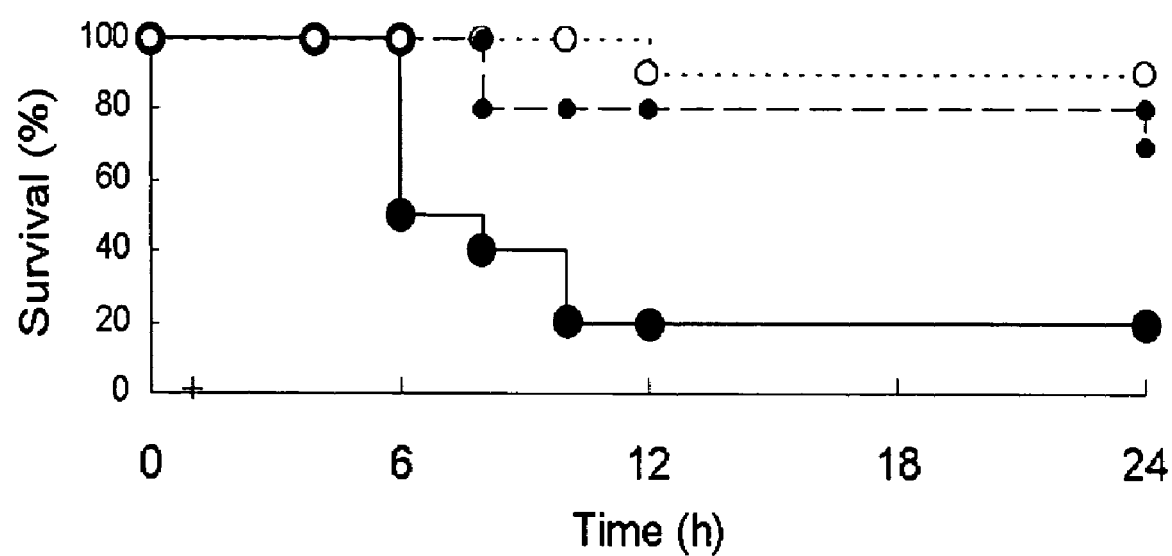
FIG. 3 shows effect of the extract obtained from the root of *Acanthopanax koreanum*, on the survival of mice in liver-injury model induced by D-GalN/LPS.

FIG. 3 or 4 shows the lethality rate of the mice induced by D-GalN/LPS, measured for 24 hours when the extract of *Acanthopanax koreanum* is administered to the said mice. More particularly, the said water extract and the said 80%-ethanol insoluble part shows excellent survival rate by more than 70~80% in 24 hours without liver toxicity. Therefore, the extract has a high efficacy such as liver protection in the mice model of the acute hepatitis. Also, FIG. 5 and FIG. 6 show that the fraction containing polysaccharide with a molecular weight larger than 100,000, among the ethanol insoluble part obtained from the root or stem of *Acanthopanax koreanum* maintains the survival rate higher than 90%, respectively. Especially, the fraction obtained from the root of *Acanthopanax koreanum* has an efficiency that when 30 mg/kg or 100 mg/kg of the said fraction was administered to the mice, the survival rate is maintained to the extent of 100%. Therefore, the fraction has an excellent efficacy for the liver protection.

FIG. 8 shows that the said ethanol insoluble part prepared by treating the said water extract with ethanol, of which the final concentration of ethanol is 80 and the fraction containing polysaccharide with a molecular weight larger than range of 12,000~14,000, among the ethanol insoluble part inhibit DNA fragmentation in liver cell.

FIG. 9 shows that the fraction containing polysaccharide with a molecular weight larger than 100,000, among the said ethanol insoluble part influences the expression of pro-apoptotic protein. Particularly, the result shows that the said fraction used in the experiment inhibits the expression of Bax protein concentration dependently. Also, in case of Bid protein which is one of pro-apoptotic proteins, experimental group to which the fraction containing polysaccharide with a molecular weight larger than 100,000 is administered, has a similar inhibition relative to the control group concentration dependently. Therefore, the said fraction containing polysaccharide with a molecular weight larger than 100,000 inhibits the expression of pro-apoptotic protein activated by TNF-$\alpha$ in liver cell.

Also, FIG. 10 and FIG. 11 show that when the 80%-ethanol insoluble part prepared by treating the water extract with ethanol is orally administered to the mice, the survival rate of the mice is maintained to the extent of 50% for 24 hours. However, the control group to which the said part is not administered is deceased within 12 hours.

Therefore, based on the working model of the acute liver-injury mice induced by D-GalN/LPS, the extract of the present invention maintains the serum level of TNF-$\alpha$, the cause of acute hepatitis, to be similar to level of the normal group. Also, the said extract inhibits the expression of pro-apoptotic protein activated by TNF-$\alpha$. Also, the said extract reduces the serum level of AST or ALT to the similar to that of normal group. Therefore, the said extract has an excellent efficacy for treatment or prevention of hepatitis, or a liver protection.

The extract of *Acanthopanax koreanum* of the present invention can be used for health supplementary food.

The extract of the present invention can be administered in various methods in an amount of dosage. The said composition contains pharmaceutically acceptable carrier. More particularly, any of pharmaceutically acceptable carrier selected from sterilized solution, or the standard carrier used in the known formulation, such as tablet, coating tablet and capsule can be used. Conservatively, carrier is selected from diluting agent containing starch, milk, glucose, clay, gelatin, stearic acid, talc, vegetable oil, gum and glycol, or the known diluting agents. Also, the said carrier can be selected from flavoring agent, pigment or another components.

To administer pharmaceutical composition containing the extract of the present invention as an effective ingredient within the said dosage, administrations can be accomplished by the conservative methods such as oral administration, intravenous injection, intramuscular injection or transdermal administration, but is not limited to them. In clinical application, the formulation can be administered through the oral or parenteral administration. The said formulation is prepared by using common diluent containing packing agent, bulking agent, bindng agent, moistening agent, disintegrating agent, surfactant or diluting agent.

Composition for oral administration can be formulated into the solid formulation such as tablet, pill, powder, granule or capsule. The said formulation is prepared by mixing one or more selected from the extract of the present invention with diluting agent for example, starch, calcium carbonate, sucrose, lactose or gelatin. Also, in addition to simple diluting agent, lubricant such as magnesium stearate is used.

Composition for oral administration can be formulated into the liquid formulation such as suspension, liquid, emulsion, syrup. The said formulation contains various diluting agent for example, moistening agent, flavoring agent, aromatic agent or preservative, in addition to simple diluent, for example water, liquid paraffin. Preferably, the composition can be formulated into the tablet, capsule, or drink, and used as medicine or health supplementary food.

Also, the pharmaceutical composition of the present invention can be parenterally administered. The formulation for parenteral administration is prepared by mixing one or more selected from the extract of the present invention with stabilizer or buffer in water, preparing into solution or suspension, and formulating into an unit dosage form such as ample or vial.

The extract used for therapeutic agent or preventor of hepatitis, or a liver protective drug is preferably the ethanol insoluble part, more preferably the fraction containing polysaccharide with a molecular weight larger than range of 12,000~14,000 among the said ethanol insoluble part. However, in the process of purification using dialyzing diaphragm, yield is 30~40%. Therefore, preferably, the ethanol insoluble part is used. An effective ingredient of the present invention can be administered through one or many times per 1 day. The dosage of the effective ingredient is preferable 1~1000 mg/kg/day, more preferable 10~1000 mg/kg/day, depending upon absorptivity of the active component in vivo, activity, excretion rate, age, sex and state of the patients, seriousness of disease under treatment. More particularly, the preferable dosage of the water extract, the 70%-ethanol insoluble part, and the fraction containing polysaccharide with a molecular weight larger than range of 12000~14000, among the said ethanol insoluble part is 300~1000 mg/kg/day, 100~500 mg/kg/day and 10~300 mg/kg/day, respectively. Accurate dosage, method and frequency for administration were selected according to property of the formulation, weight and state of administrative group, or characteristic of derivatives used.

Toxic test for the mice shows that the extract of the present invention, obtained from the root or stem of *Acanthopanax koreanum* is nontoxic. Also, the test shows that LD50 is higher than 2000 mg/kg, the extract of the present invention has high safety and stability. Therefore, the extract of the present invention, as a liver protective drug can be safely administered to the body.

The present invention will be explained in more detail with reference to the following examples. However the following examples are provided only to illustrate the present invention, and the present invention is not limited to them.

EXAMPLE 1

Preparation of the Water Extract of *Acanthopanax koreanum*

The root or stem of *Acanthopanax koreanum* is dried and sliced to small pieces, respectively. In a 10 L flask, 1 kg of slices was mixed with water and extracted at the temperature more than 90° C. for 3 hours. The extraction is repeated two times. The extract is filtered through the filtrate membrane, concentrated under reduced pressure and lyophilized to prepare the water extract. Quantity of the water extract obtained from the root or stem of *Acanthopanax koreanum* is 142 g or 80 g, respectively.

EXAMPLE 2

Preparation of the Ethanol Insoluble Part of *Acanthopanax koreanum*

The ethanol insoluble part containing more polysaccharide relative to the said water extract was prepared by treating the said water extract with ethanol. 20 g of the said water extract obtained from the root or stem of *Acanthopanax koreanum* was dissolved in 50 ml of water. Ethanol was added to the solution, of which final concentration of ethanol was 60~80%. The solution was centrifuged to acquire the precipitated insoluble part. The insoluble part was dried.

Also, the ethanol filtrate after centrifugal separation was concentrated to acquire the ethanol extract from the said water extract obtained from the root or stem of *Acanthopanax koreanum*, respectively. Quantity of the ethanol insoluble part and ethanol extract obtained by treating the water said extract of the root or stem of *Acanthopanax koreanum* with ethanol was shown in the table 1.

TABLE 1

| | | Quantity of the ethanol insoluble part and the ethanol extract | | | |
|---|---|---|---|---|---|
| Final Conc. of ethanol | Quantity of the water extract(g) | Root | | Stem | |
| | | SRWB[a](g) | SRWS[b](g) | SSWB[c](g) | SSWS[d](g) |
| 60% | 20 | 4.5 | 15.3 | 3.7 | 16.5 |
| 70& | 20 | 6.9 | 13.5 | 5.1 | 15.2 |
| 80% | 20 | 8.6 | 11.4 | 5.6 | 14.9 |

[a]the ethanol insoluble part of the water extract obtained from the root of *Acanthopanax koreanum*(hereinafter, abbreviated into SRWB)
[b]the ethanol soluble part of the water extract obtained from the root of *Acanthopanax koreanum*(hereinafter, abbreviated into SRWS)
[c]the ethanol insoluble part of the water extract obtained from the stem of *Acanthopanax koreanum*(hereinafter, abbreviated into SSWB)
[d]the ethanol soluble part of the water extract obtained from the stem of *Acanthopanax koreanum*(hereinafter, abbreviated into SSWS)

As shown in the table 1, in case of treating the water extract with ethanol, the yield of ethanol insoluble part was higher when final concentration of ethanol is 80% than when final concentration of ethanol is 60% or 70%.

EXAMPLE 3

Preparation of the Fraction Containing Polysaccharide with a Molecular Weight Larger than Range of 12,000~14,000, Among the said Ethanol Insoluble Part The ethanol insoluble part obtained by treating the water extract with ethanol has polysaccharide as the major component. However, to purify the said polysaccharide, the fraction containing polysaccharide with a molecular weight larger than range of 12000~14000 is prepared by dialysis of the said extract through dialyzing diaphagram (Spectra Por Spectrum Medical Industries Inc. Houston Tex.) corresponding to the molecular weight, respectively.

The water extract obtained from the root or stem of *Acanthopanax koreanum* was treated with 80% ethanol to prepare the ethanol insoluble part, respectively. The 500 mg of the said ethanol insoluble part was dissolved in 7 ml of distilled water, thereafter the solution was centrifuged to acquire the supernatant. The said supernatant was dialysed through the dialyzing diaphagram passing the compound with a molecular weight in the range of 12000~14000, thereafter filter cake was lyophilized. Quantity of the fraction containing polysaccharide with a molecular weight larger than range of 12000~14000, obtained from the 300 mg of the ethanol insoluble part prepared from the root or stem of *Acanthopanax koreanum* is 130 mg or 120 mg, respectively.

EXAMPLE 4

Preparation of the Fraction Containing Polysaccharide with a Molecular Weight Larger than 100,000, Among the said Ethanol Insoluble Part To purify the polysaccharide of *Acanthopanax koreanum* additionally, the fraction containing polysaccharide with a molecular weight larger than 100,000 is prepared by filtering the said extract through dialyzing diaphagram (Spectra Por Spectrum Medical Industries Inc. Houston Tex.) passing the compound with a molecular weight smaller than 100,000.

The water insoluble part obtained from the root or stem of *Acanthopanax koreanum* was treated with ethanol to prepare the ethanol extract. 15.5 g or 20.7 g of the ethanol insoluble part was dissolved in the water, respectively. The solution was dialysed through the dialyzing diaphagram passing the compound with a molecular weight smaller than 100,000, thereafter filter cake was lyophilized. Yield of the fraction containing polysaccharide with a molecular weight larger than 100,000, obtained from the ethanol insoluble part prepared from the root or stem of *Acanthopanax koreanum* is 12% or 10.2%, respectively.

The experiment confirming that the extract of the present invention has efficiency for treatment of hepatitis or liver protection in liver-injury mice model induced by D-GalN/LPS was accomplished as shown in the below.

EXPERIMENTAL EXAMPLE 1

HPLC Analysis of the Fraction Containing Polysaccharide

As for the fraction containing polysaccharide with a molecular weight larger than range of 12,000~14,000, obtained from the said ethanol insoluble part, molecular weight or number of the polysaccharide was measured.

Figure 1:
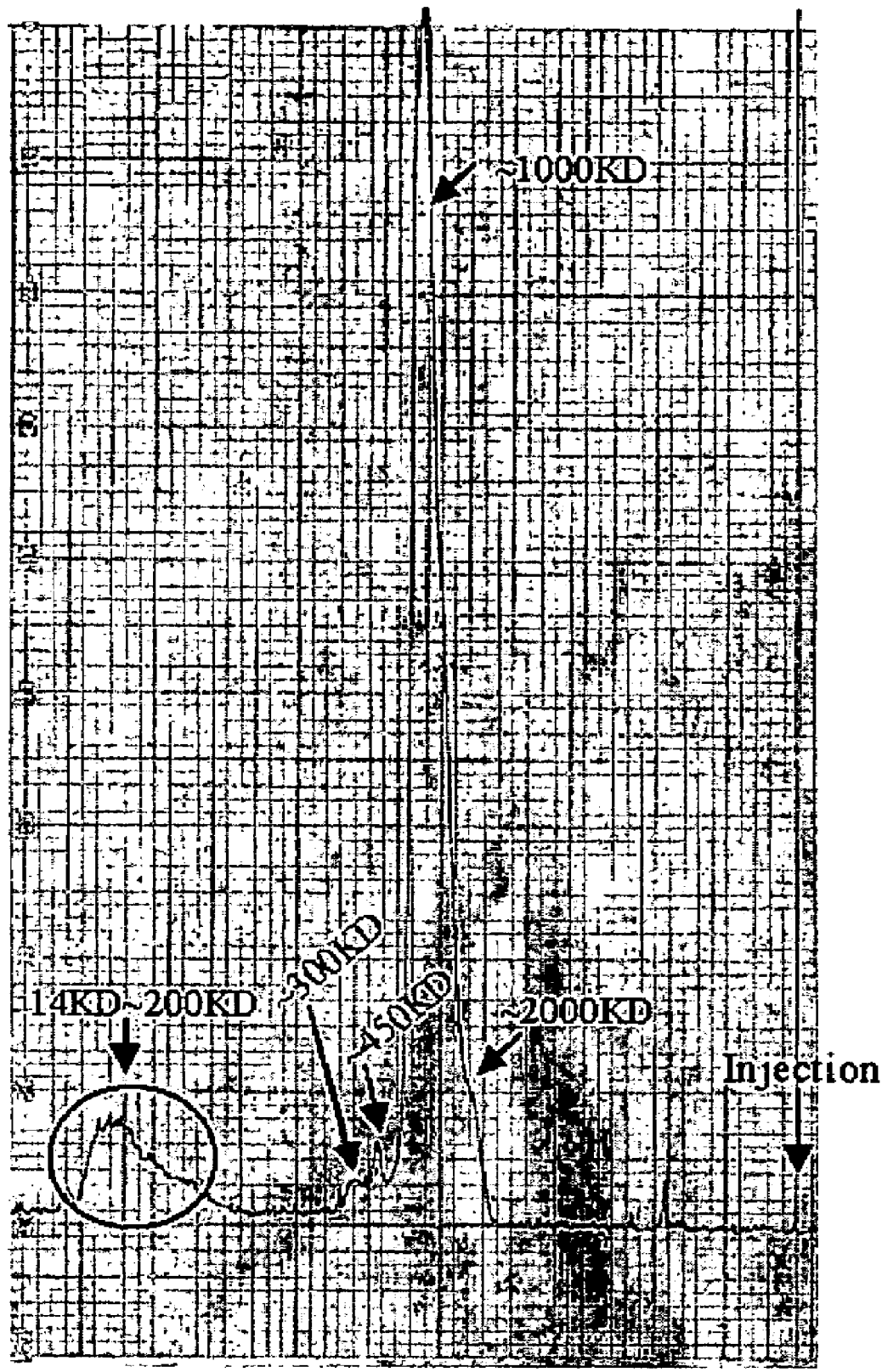
FIG. 1 shows HPLC analysis of the fraction containing polysaccharide with a molecular weight larger than range of 12,000~14,000, among the ethanol insoluble part, obtained from the root of *Acanthopanax koreanum*
Figure 2:
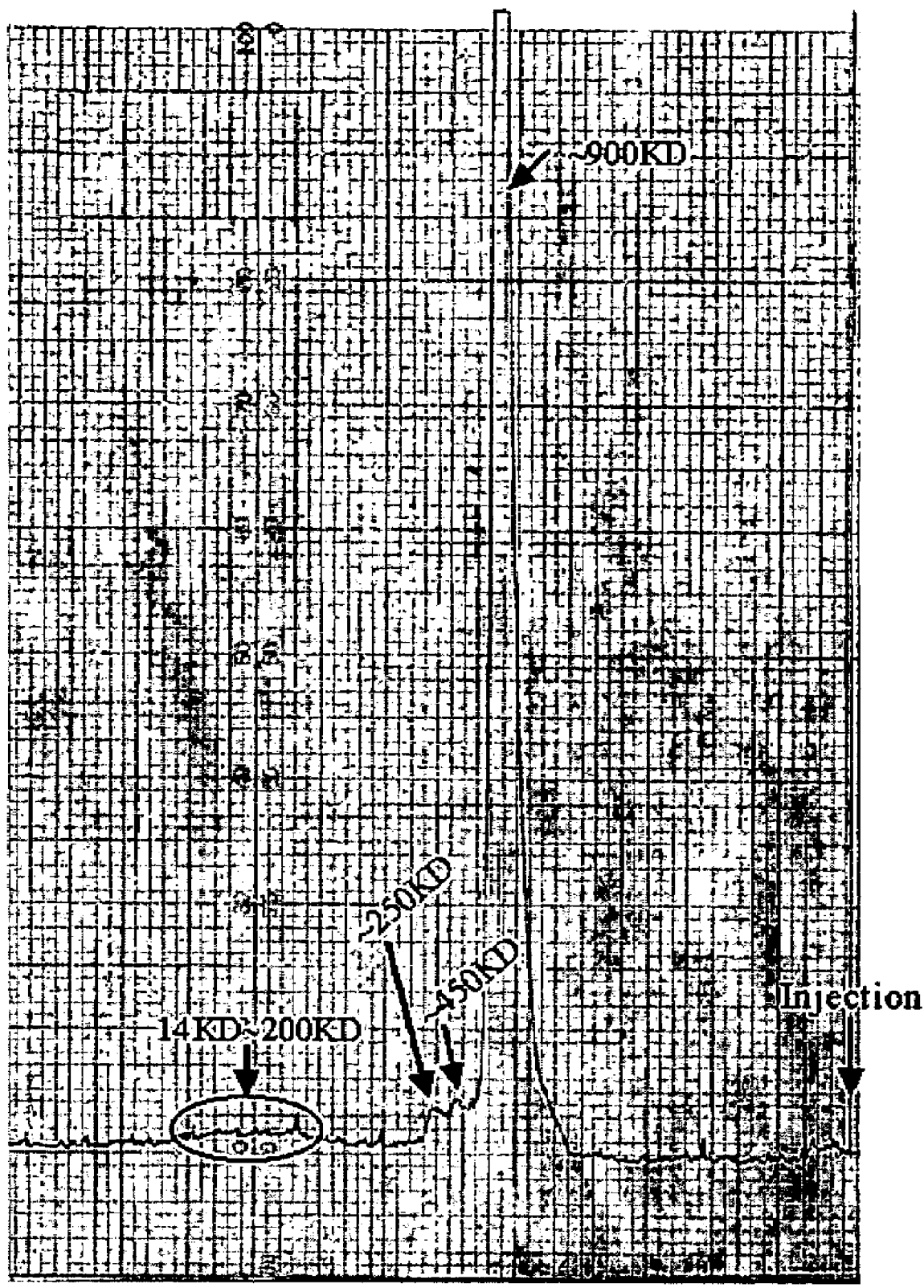
FIG. 2 shows HPLC analysis of the fraction containing polysaccharide with a molecular weight larger than range of 12,000~14,000, among the ethanol insoluble part, obtained from the stem of *Acanthopanax koreanum*.

The fraction containing polysaccharide with a molecular weight larger than range of 12,000~14,000, obtained from the root or stem of *Acanthopanax koreanum* was dissolved in the distilled water, of which the final concentration of polysaccharide was 10 mg/ml. 20 µl of the solution was injected to YMC-pack Diol-300 column (YMC Co. Kyoto, Japan). The elution rate of eluent is 1 ml/min. Molecular weight and number of the polysaccharide in the sample were analyzed by evaporation light scattering detector (Alltech 500 ELSD) (shown in FIG. 1 or FIG. 2).

The extract containing polysaccharide, obtained from the stem of *Acanthopanax koreanum* is mainly comprised of polysaccharide with a molecular weight 900,000. Also, polysaccharide with a various molecular weight, for example, 450,000 or 250,000 was contained in the extract. Also, polysaccharide with a molecular weight in the range of 14,000~200,000 was contained in the extract. The extract containing polysaccharide, obtained from the root of *Acanthopanax koreanum* is mainly comprised of polysaccharide with a molecular weight more than 1,000,000. Also, polysaccharide with a various molecular weight, for example, 2,000,000, 450,000 or 300,000 was contained in the extract. More polysaccharide with a molecular weight in the range of 14,000~200,000 was contained in the extract of the root than that of the stem.

EXPERIMENTAL EXAMPLE 2

The Serum Level of AST or ALT in Liver-Injury Mice Model Induced by D-GalN/LPS

The experiment confirming that the extract of the present invention has a efficacy for prevention of hepatitis in liver-injury mice model induced by D-GalN/LPS by measuring the serum level of AST or ALT was accomplished as shown in the below.

After mice (B57BL/6) having body weights of 20 g were adjusted to a new environment for 1 week, they were used in the experiment. Mice were fully fed before the experiment. The experiment was accomplished with mice divided to three groups such as normal group, group to which physiological saline solution was administered (physiological saline solution-treated group), group to which the extract was administered (the extract-treated group). The said extract was selected from the group consisting of 1) the methanol extract obtained by treating the root or stem of Acanthopanax koreanum with 100% methanol, 2) the water extract of Acanthopanax koreanum obtained by treating the root or stem of Acanthopanax koreanum with water, 3) the ethanol extract obtained by treating the root or stem of Acanthopanax koreanum with 70% ethanol 4) the ethanol insoluble part among the said water extract, obtained by treating the said water extract with ethanol, of which final concentration of ethanol is 80%, or 5) the fraction containing polysaccharide with a molecular weight larger than range of 12,000~14,000 among the ethanol insoluble part.

The said extract dissolved in physiological saline solution was intraperitoneally administered to the said mice model twice in an amount of 50 mg/kg or 300 mg/kg, respectively, at 12 and 1 hour earlier than D-Gal and LPS treatment. Thereafter, D-Gal and LPS were subsequently administered to the said mice model in an amount of 700 mg/kg and 10 mg/kg, respectively.

Physiological saline solution was administered to the control group of the said mice model in the same amount. Blood was collected from the mice at 8 hours after administration. DNA was isolated from the part of liver tissue. The part of liver was maintained in 10% formalin for staining of tissue. The collected blood was centrifuged at 3000 rpm, the serum was isolated and stored at −20° C. The serum level of AST and ALT was measured by using kit purchased from the ARKARY FACTORY (JAPAN) and auto-dry chemistry analyzer (SPOTCHEM, ARKARY, JAPAN) to measure the serum level of GOT and GPT in blood. The result was shown in table 2 and 3.

TABLE 2

The effect of the various root extract of Acanthopanax koreanum on the serum level of AST and ALT in liver-injury mice model induced by D-GalN/LPS

| Group | Amount (mg/kg) | AST | ALT |
|---|---|---|---|
| Normal group | — | 67 ± 11 | 23 ± 11 |
| Physiological saline solution-treated group (control group) | — | 3456 ± 1064 | 3678 ± 1291 |
| The water extract-treated group | 50 | 567 ± 181 | 548 ± 139 |
|  | 300 | 190 ± 40 | 117 ± 47 |
| The 70% ethanol extract-treated group | 50 | 678 ± 125 | 598 ± 217 |
|  | 300 | 228 ± 45 | 96 ± 33 |
| Treatment of the water extract with ethanol | The ethanol insoluble part-treated group | 50 | 378 ± 113 | 364 ± 128 |
|  |  | 300 | 189 ± 45 | 143 ± 53 |
|  | The ethanol soluble part-treated group | 50 | 589 ± 139 | 543 ± 145 |
|  |  | 300 | 450 ± 120 | 425 ± 107 |
| The fraction containing polysaccharide with a molecular weight larger than range of 12,000~14,000 | 50 | 127 ± 35 | 118 ± 31 |
| The fraction containing polysaccharide with a molecular weight larger than 100,000 | 30 | 125 ± 32 | 97 ± 35 |
|  | 100 | 92 ± 25 | 76 ± 30 |

The said result derives from mean ± SEM of measurements obtained from the experiments of five times, five times and six times as for normal group, saline solution-treated group and the extract-treated group, respectively.

TABLE 3

The effect of the various stem extract of Acanthopanax koreanum on the serum level of AST and ALT in liver-injury mice model induced by D-GalN/LPS.

| Group | Amount (mg/kg) | AST | ALT |
|---|---|---|---|
| Normal group | — | 67 ± 11 | 23 ± 11 |
| Physiological saline solution-treated group(control group) | — | 3456 ± 1064 | 3678 ± 1291* |
| The water extract-treated group | 50 | 598 ± 194 | 634 ± 157 |
|  | 300 | 165 ± 13 | 26 ± 13 |
| The 70% ethanol extract-treated group | 50 | 2987 ± 1859 | 3125 ± 1032 |
|  | 300 | 3283 ± 1959 | 3457 ± 2373 |
| Treatment of the water extract with ethanol | The ethanol insoluble part-treated group | 50 | 446 ± 115 | 464 ± 167 |
|  |  | 300 | 131 ± 11 | 19 ± 11 |
|  | The ethanol soluble part-treated group | 50 | 550 ± 104 | 567 ± 134 |
|  |  | 300 | 523 ± 130 | 543 ± 145 |
| The fraction containing polysaccharide with a molecular weight larger than range of 12,000~14,000 | 50 | 121 ± 14 | 26 ± 11 |
| The fraction containing polysaccharide with a molecular weight larger than 100,000 | 30 | 112 ± 15 | 32 ± 12 |
|  | 100 | 91 ± 12 | 21 ± 15 |

The said result derives from mean ± SEM of measurements obtained from the experiments of five times, five times and six times as for normal group, saline solution-treated group and the extract-treated group, respectively.

As shown in the table 2 and 3, the serum level of AST and ALT in mice model, which administered only saline with D-GalN/LPS was markedly increased relative to that of the normal group.

Also, the serum level of AST and ALT in mice model, which administered the 70% ethanol extract or the supernatant prepared by treating the water extract with 80% ethanol was similar to that of the physiological saline solution-treated group. Therefore, it was shown that the 70% ethanol extract and the supernatant have no efficiency for the treatment of hepatitis.

However, the serum level of AST and ALT in mice model, which administered 50 mg/kg of the water extract was decreased greatly relative to that of the physiological saline solution-treated group. The serum level of AST and ALT in mice model, which administered the 80%-ethanol insoluble part was more decreased. More preferably, the serum level of AST and ALT in mice model, which administered 50 mg/kg of the fraction containing polysaccharide with a molecular weight larger than range of 12,000~14,000, among the ethanol insoluble part was the lowest one of all, and was similar to the that of normal group. The said fraction has excellent efficacy for treatment of hepatitis.

EXPERIMENTAL EXAMPLE 3

The Serum Level of TNF-α of the Extract on the Liver-Injury Mice Model Induced by D-GalN/LPS The experiment measuring the serum level of TNF-α, direct mediator of acute hepatitis in liver-injury mice model induced by D-GalN/LPS was accomplished as shown in the below.

After mice (B57BL/6) having body weights of 20 g were adjusted to a new environment for 1 week, they were used in experiment. Mice were fully fed before the experiment. The experiment was accomplished with mice divided to three groups such as normal group, group to which physiological saline solution was administered (physiological saline solution-treated group), group to which the extract was administered (the extract-treated group). The extract was administered to the mice in the same method as the experimental example 2.

The said extract dissolved in physiological saline solution was intraperitoneally administered to the mice in an amount of 50 mg/kg or 300 mg/kg for two times, respectively. Thereafter D-Gal and LPS were subsequently administered to the mice in an amount of 700 mg/kg and 10 mg/kg.

Physiological saline solution was administered to the mice in the same amount. Blood was collected from mice at 1 hour after administration. The collected blood was kept at the room temperature for 1 hour and centrifuged, the serum was isolated. The prepared serum and liver were stored at −20° C.

The serum level of TNF-α was measured by using enzyme-linked immunosorbent assay (ELISA) kit. The result was shown in table 4 and 5.

TABLE 4

The effect of various extracts of *Acanthopanax koreanum* root on the serum level of TNF-α in liver-injury mice model induced by D-GalN/LPS.

| Group | | Amount(mg/kg) | TNF-α (pg/ml) |
|---|---|---|---|
| Normal group | | — | 26 ± 13 |
| Physiological saline solution-treated group(control group) | | — | 678 ± 29 |
| The water extract-treated group | | 50 | 124 ± 36 |
| | | 300 | 74 ± 26 |
| The 70% ethanol extract-treated group | | 50 | 648 ± 104 |
| | | 300 | 587 ± 87 |
| Treating the water extract with ethanol | The ethanol insoluble part-treated group | 50 | 102 ± 26 |
| | | 300 | 59 ± 15 |
| | The ethanol soluble part-treated group | 50 | 605 ± 92 |
| | | 300 | 260 ± 45 |
| The fraction containing polysaccharide with a molecular weight larger than range of 12,000~14,000 | | 50 | 32 ± 12 |
| The fraction containing polysaccharide with a molecular weight larger than 100,000 | | 30 | 45 ± 21 |
| | | 100 | 29 ± 12 |

The said result derives from mean ± SEM of measurements obtained from the experiments of five times, five times and six times as for normal group, physiological saline solution-treated group and the extract-treated group, respectively.

TABLE 5

The effect of various extracts of *Acanthopanax koreanum* stem on the serum level of TNF-α in liver-injury mice model induced by D-GalN/LPS.

| Group | | Amount(mg/kg) | TNF-α (pg/ml) |
|---|---|---|---|
| Normal group | | — | 26 ± 11 |
| Physiological saline solution-treated group(control group) | | — | 785 ± 17 |
| The water extract-treated group | | 50 | 132 ± 28 |
| | | 300 | 67 ± 16 |
| The 70% ethanol extract-treated group | | 50 | 690 ± 110 |
| | | 300 | 678 ± 54 |
| Treating the water extract with ethanol | The ethanol insoluble part-treated group | 50 | 62 ± 16 |
| | | 300 | 566 ± 55 |
| | The ethanol soluble part-treated group | 50 | 233 ± 43 |
| | | 300 | 28 ± 11 |
| The fraction containing polysaccharide with a molecular weight larger than range of 12,000~14,000 | | 50 | 32 ± 12 |
| The fraction containing polysaccharide with a molecular weight larger than 100,000 | | 30 | 32 ± 12 |
| | | 100 | 25 ± 11 |

The said result derives from mean ± SEM of measurements obtained from the experiments of five times, five times and six times as for normal group, saline solution-treated group and the extract-treated group, respectively.

As shown in the table 4 and 5, the serum level of TNF-α in mice to which D-GalN/LPS was only administered except the extract was increased thirty times as much as that of the normal group.

The serum level of TNF-α in mice to which 300 mg/kg of the water extract was administered was decreased.

More preferably, the serum level of TNF-α in mice to which the 80%-ethanol insoluble part of the water extract was administered was the most similar to that of normal group. The said 80%-ethanol insoluble part has an excellent efficacy for treatment of hepatitis.

EXPERIMENTAL EXAMPLE 4

Effect of the Extract on the Survival of the Liver-Injury Mice Model Induced by D-GalN/LPS The experiment measuring survival of liver-injury mice model induced by D-GalN/LPS was accomplished for 24 hours as shown in the below.

After mice (B57BL/6) having body weights of 20 g were adjusted to a new environment for 1 week with normal diet, they were used in experiment. Mice were starved for twenty hours before the experiment. Thereafter, 700 mg/kg of D-Gal and 10 mg/kg of LPS were administered to the mice. Liver-injury mice model induced by D-GalN/LPS was prepared for the experiment. The experiment was accomplished with mice divided to three groups such as normal group, group to which saline solution was administered, group to which the extract was administered. The said extract is the water extract obtained by treating the root or stem of *Acanthopanax Koreanum* with water, the 80%-ethanol insoluble part among the said water extract, or the fraction containing polysaccharide with a molecular weight larger than 100,000 among the said 80%-ethanol insoluble part.

Physiological saline solution was administered to the mice in the same amount.

1. The Effect of the said Water Extract or the said 80%-Ethanol Insoluble Part on the Lethality Rate of the Mice.

The said water extract or the said 80%-ethanol insoluble part dissolved in physiological saline solution was administered to the mice in an amount of 50 mg/kg or 300 mg/kg, respectively. Thereafter, lethality rate was measured for 24 hours after administration.

FIG. 3 shows that the water extract obtained from the root of *Acanthopanax koreanum* decreased the lethality of the mice induced by D-GalN/LPS. Group to which physiological saline solution was administered was diseased at 6 hours after D-GalN/LPS. All of the group (eight mice) was diseased within 24 hours.

However, seven of ten mice to which 300 mg/kg of the water extract was administered survived within 24 hours, then the survival rate resulted in 80%. Nine of ten mice to which 300 mg/kg of the said 80%-ethanol insoluble part was administered survived within 24 hours, then the survival rate resulted in 90%.

FIG. 4 shows that the water extract obtained from the stem of *Acanthopanax koreanum* decreased the lethality of the mice induced by D-GalN/LPS. Group to which physiological saline solution was administered was diseased at 6 hours after D-GalN/LPS. Nine mice of the group (ten mice) were diseased within 24 hours.

However, seven of ten mice to which 300 mg/kg of the water extract was administered survived within 24 hours, then the survival rate resulted in 70%. Nine of ten mice to which 300 mg/kg of the said 80%-ethanol insoluble part was administered survived within 24 hours, then the survival rate resulted in 90%.

The said result shows that the said water extract or the said ethanol insoluble part obtained from the root or stem of *Acanthopanax koreanum* made the survival rate maintained in the range of 70%~90%. Therefore, the water extract or the 80%-ethanol insoluble part has an efficacy for a liver protection.

2. The Effect of the Polysaccchardie Fraction with Molecular Weight Larger than 100,000 on the Lethality Rate of the Mice.

The water extract dissolved in physiological saline solution was intraperitoneally administered to the mice in an amount of 30 mg/kg or 100 mg/kg for two times, respectively. Thereafter, lethality rate was measured after administration.

700 mg/kg of D-GalN and 10 mg/kg of LPS was administered to the mice, thereafter the fraction containing polysaccharide with a molecular weight larger than 100,000, among the ethanol insoluble part was administered to the mice in an amount of 30 mg/kg or 100 mg/kg, respectively. Thereafter, lethality rate was measured for 24 hours after administration.

FIG. 5 shows that the water extract obtained from the stem of *Acanthopanax koreanum* decreased the lethality rate of the mice induced by D-GalN/LPS. Group to which physiological saline solution was administered was diseased at 5 hours after administration of D-GalN/LPS. Also, lethality rate reached 84% (ten of twelve mice were diseased.) at 6 hours after administration. Lethality rate reached 92% (eleven of twelve mice were diseased.) at 15 hours after administration.

However, lethality rate of mice to which 30 mg/kg or 100 mg/kg of the fraction containing polysaccharide with a molecular weight larger than 100,000, obtained from the stem of *Acanthopanax koreanum* was administered reached 16% (two of twelve mice were diseased.) or 8% (one of twelve mice were diseased.) at 24 hours after administration, respectively. Therefore, the fraction has an efficacy for a liver protection.

As shown in FIG. 6, mice to which the said fraction was not administered was diseased at 5 hours after administration of D-GalN/LPS. Also, lethality rate reached 86% (six of seven mice were diseased.) at 6 hours after administration. Lethality rate reached 100% (all of twelve mice were diseased.) at 7 hours after administration.

However, lethality rate of mice to which 30 mg/kg or 100 mg/kg of the fraction containing polysaccharide with a molecular weight larger than 100,000, obtained from the stem of *Acanthopanax koreanum* was administered reached 0% (all of twelve mice were diseased.).

EXPERIMENTAL EXAMPLE 5

Effect of the Extract on the Survival of the Liver-Injury Mice Model Induced by D-GalN/TNF-α

To confirm whether liver protection of the *Acanthopanax koreanum* is directly connected to the inhibition of LPS-induced production of TNF-α or inhibition of signaling pathway through TNF-α receptor or not, the experiment was accomplished at the same procedure of the said experiment with intravenous administration of TNF-α in an amount of 15 µg/kg instead of LPS. Therefore, acute liver-injury mice model induced by D-GalN/TNF-α were prepared for the experiment.

For the experiment, the fraction containing polysaccharide with a molecular weight larger than 100,000, displaying the most excellent survival in the said experiment 5, was administered to the said mice. In case of control group, physiological saline solution was only administered to the mice. Six mice per group were used for the experiment. TNF-α was intravenously administered to the mice and then immediately D-GalN was intraperitoneally administered.

The fraction was administered to the mice at 12 hours and 1 hour before administration of D-GalN/TNF-α. The result was shown in FIG. 7. Five of six mice of the control group were diseased at 6 hours after administration of D-GalN/TNF-α, then lethality rate reached 83%. However, one of six mice of the administrative group were diseased to 8 hours after administration of D-GalN/TNF-α, then lethality rate reach 17%. Therefore, the fraction containing polysaccharide show the high survival in mice to which TNF-α was directly administered.

EXPERIMENTAL EXAMPLE 6

Measurement of DNA Fragmentation in Liver Cell

The experiment confirming whether the extract inhibits apoptosis of liver cell in the liver-injury mice model induced by D-GalN/LPS was accomplished as shown in the below.

DNA was isolated from the liver tissue of the mice. Electrophoresis of the isolated DNA was accomplished, thereafter electro gel was dyed with ethidium bromide to confirm whether DNA was fragmented or not.

FIG. 8 show that electrophoresis of DNA (3) and (4) isolated from the mice to which 300 mg/kg of the water extract obtained from the root or stem of *Acanthopanax koreanum* was administered was similar to one of DNA (1) isolated from the mice to which physiological saline solution was administered. Preferably, electrophoresis of DNA (5) isolated from the mice to which 300 mg/kg of the ethanol insoluble part obtained from the root or stem of *Acanthopanax koreanum* was administered shows that the said part has an efficacy to inhibit DNA fragmentation of liver cell in the liver-injury mice model induced by D-GalN/LPS. Furthermore, the fraction containing polysaccharide with a molecular weight larger than range of 12,000~14,000 inhibits the fragmentation of DNA induced by D-GalN/LPS. Therefore, the extract of *Acanthopanax koreanum* of the present invention inhibits the fragmentation of DNA induced by D-GalN/LPS, thus has an efficacy to inhibit apoptosis of liver cell.

EXPERIMENTAL EXAMPLE 7

The Effect of the Fraction Containing Polysaccharide with a Molecular Weight Larger than 100,000 on the Expression of Pro-Apoptotic Protein.

The experiment confirming whether the fraction containing polysaccharide with a molecular weight larger than 100,000 inhibits expression of pro-apoptotic proteins such as Bid or Bax, which play an important role in apoptosis of liver cell by D-GalN/LPS, was accomplished as shown in the below.

700 mg/kg of D-GalN and 10 mg/kg of LPS were intraperitoneally administered to the mice. The fraction or physiological saline solution was intraperitoneally administered to the mice at 12 hours and 1 hour before administration of D-GalN/LPS. The said fraction was administered to the mice in amount of 10 mg/kg, 30 mg/kg or 100 mg/kg. Liver cell isolated from the mice to which the said fraction or physiological saline solution was administered was added to lysis buffer solution (prepared by mixing 50 mM Tris-HCl, 1% Nonidet P-40, 1 mM EDTA, 1 mM phenylmethyl sulfonyl flurioride, 1 g/ml leupeptin with 150 mM NaCl, pH 7.5), then homogenized and centrifuged at 15,000 xg for 10 mm to prepare crude protein. Total concentration of protein was measured by using Bradford method. 50 □ of protein was loaded at 12%~15% sodium dodecyl sulfate polyacrylamide gel. After electrophoration the said gel was transferred to PVDF membrane (Millipore, Bedford, Mass. USA). The membrane was incubated for 3 hours in the solution prepared by mixing Tris-buffered saline solution and 0.1% Tween 20(Sigma corp.) and adding 5% skim milk. Then, primary antibody such as rabbit polyclonal anti-Bax antibody (Santa Cruz Biochemicals, Santa Cruz, Calif. USA) or anti-Bid antibody (Santa Cruz Biochemicals, Santa Cruz, Calif. USA) was incubated in the said membrane. Thereafter, the membrane was washed with buffered saline for 15 mm and three times. Thereafter, secondary antibody was incubated in the membrane for 1 hour. The membrane was washed. Expression of protein was measured with Amersham ECL system (Amersham Pharmacia Biotec, Buckinghamshire, UK).

FIG. 9 shows that the fraction containing polysaccharide with a molecular weight larger than 100,000 inhibited expression of Bax, pro-apoptotic protein concentration dependently. Also, the expression of Bid, pro-apoptotic protein in the fraction-treated group was similar to that of Bid in normal group concentration dependently. However, in case of the mice to which physiological saline solution was administered, expression of Bid was decreased relative to the result of normal group. Therefore, the fraction containing polysaccharide with a molecular weight larger than 100,000 inhibits activation or expression of pro-apoptotic protein induced by liver-injury in liver cell. Consequently, the fraction has an efficacy on the liver protection.

EXPERIMENTAL EXAMPLE 8

Liver Protection in Oral Administration of the Extract of *Acanthopanax koreanum* to the Mice The experiment confirming whether the 80%-ethanol insoluble part among the water extract has an efficiency for liver protection for oral administration was accomplished as shown in the below.

The said 80%-ethanol insoluble part was dissolved in water. The solution was orally fed the mice in an amount of 100 mg/kg or 300 mg/kg per day. D-GalN/LPS was administered to the mice at one week after administration of the said part. The lethality rate was measured for 24 hours. As for control group to which the said part was not administered, the lethality rate was measured for 24 hours.

As shown in FIG. 10 and 11, the control group was diseased at 6 hours after administration of D-GalN/LPS. All the mice of the control group were diseased at 12 hours after administration of D-GalN/LPS. However, three of six mice to which 300 mg/kg of the said ethanol insoluble part was administered survived at 24 hours after administration of D-GalN/LPS.

The said 80%-ethanol insoluble part inhibits the formation of TNF-α and expression of various pro-apoptotic proteins. Therefore, the said ethanol insoluble part has an efficacy for the liver protection.

EXPERIMENTAL EXAMPLE 9

Acute Toxicity in Oral Administration of the Extract of *Acanthopanax koreanum* to the Mice The experiment confirming whether the extract of the present invention has acute toxicity or not was accomplished as shown in the below.

As for the experimental group comprising of five or six mice (B57BL/6) having body weights of 20 g, the experiment confirming whether the extract of the present invention has acute toxicity or not was accomplished. The 80%-ethanol insoluble part among the water extract of *Acanthopanax koreanum* prepared in example 2 was orally administered to the experimental group in an amount of 2000 mg/kg, thereafter toxification of the experimental group was observed for 7 days. Particularly, death, clinic symptoms, change of body weight of the mice were observed after administration of the said part. Also, hematological test and biochemical test of blood were accomplished. The mice were autopsied to test abnormality of abdominal cavity or pleural cavity. In the group to which the said part was administered, abnormality of change of body weight, clinic symptoms, result of hematological test, biochemical test of blood, and autopsy was not observed. Also, the mice were not diseased.

The said ethanol insoluble part causes no toxic effect in all of the mice. LD50 for oral administration is 2000 mg/kg. Therefore, the said ethanol insoluble part has high stability in the mice body. Also, the said ethanol insoluble part was safely administered to the body to protect liver.

INDUSTRIAL APPLICABILITY

The said extract of the present invention has efficacy illustrated in the below.

First, the present invention provides 1) the water extract of *Acanthopanax koreanum* obtained by treating the root or stem of *Acanthopanax koreanum* with water, 2) the ethanol insoluble part among the said water extract, obtained by treating the said water extract with ethanol, 3) the fraction containing polysaccharide with a molecular weight larger than range of 12,000~14,000, among the said ethanol insoluble part, or 4) the fraction containing polysaccharide with a molecular weight larger than 100,000, among the said ethanol insoluble part.

Second, the extract of the present invention reduces the serum level of AST, ALT and TNF-$\alpha$ in liver-injury mice model induced by D-GalN/LPS to be similar to ones of normal group also, the extract of the present invention inhibits expression of pro-apoptotic protein of liver cell activated by TNF-$\alpha$. Third, the extract of the present invention inhibits that DNA in liver cell is cleaved to the small fragments.

Forth, the extract of the present invention made high survival rate more than 90%, maintained in the experiment for measurement of lethality rate progressed for 24 hours. Also, the extract of the present invention has no toxic effects in histological test. Therefore, the extract of the present invention can be used as therapeutic agent or preventor of the hepatitis, or a liver protective drug.

What is claimed is:

1. An ethanol insoluble part derived from a water extract of the root or stem of *Acanthopanax koreanum* for treatment of hepatitis or protection of liver by inhibiting apoptosis of a liver cell, wherein the ethanol insoluble part is comprised of polysaccharide with a molecular weight larger than the range of 12,000~14,000, and,
   wherein said ethanol insoluble part is prepared by a process comprising the steps of:
   1) obtaining said water extract of the root or stem of *Acanthopanax koreanum* prepared by extracting *Acanthopanax koreanum* with water;
   2) adding ethanol to the water solution to produce the aqueous ethanol solution, wherein the final concentration of ethanol in the aqueous ethanol solution is between 50% and 90%;
   3) centrifuging the aqueous ethanol solution to precipitate; and,
   4) filtering the ethanol insoluble part precipitated in the aqueous ethanol solution to obtain the ethanol insoluble part.

2. The ethanol insoluble part of claim 1, wherein said ethanol insoluble part is comprised of polysaccharide with a molecular weight larger than 100,000.

3. The ethanol insoluble part of claim 1, wherein the final concentration of ethanol in step 3) is 80%.

4. A pharmaceutical composition for the treatment of hepatitis containing the ethanol insoluble part of any of claims 1, 2 and 3.

5. A pharmaceutical composition for protection of liver by inhibiting apoptosis containing the ethanol insoluble part of any of claims 1, 2 and 3.

6. A TNF-$\alpha$ inhibitor containing the ethanol insoluble part of any of claims 1, 2 and 4.

7. A Health supplementary food containing the ethanol insoluble part of any of claims 1, 2 and 4.

* * * * *